United States Patent
Pierson, III

(10) Patent No.: US 6,663,633 B1
(45) Date of Patent: Dec. 16, 2003

(54) HELICAL ORTHOPEDIC FIXATION AND REDUCTION DEVICE, INSERTION SYSTEM, AND ASSOCIATED METHODS

(76) Inventor: Raymond H. Pierson, III, 808 McIntyre Ave., Winter Park, FL (US) 32789

( * ) Notice: Subject to any disclaimer, the term of this patent is extended or adjusted under 35 U.S.C. 154(b) by 331 days.

(21) Appl. No.: 09/697,451

(22) Filed: Oct. 26, 2000

(51) Int. Cl.$^7$ .................... A61B 17/56; A61B 17/04; A61B 17/08
(52) U.S. Cl. .................... 606/72; 606/148; 606/216
(58) Field of Search .................. 606/71, 72, 73, 606/213, 216, 144, 148

(56) References Cited

U.S. PATENT DOCUMENTS

| | | | |
|---|---|---|---|
| 5,582,616 A | * 12/1996 | Bolduc et al. | 606/143 |
| 5,662,683 A | * 9/1997 | Kay | 606/232 |
| 5,810,851 A | * 9/1998 | Yoon | 606/148 |
| 5,810,882 A | * 9/1998 | Bolduc et al. | 606/213 |
| 5,904,696 A | * 5/1999 | Rosenman | 606/151 |
| 6,113,611 A | * 9/2000 | Allen et al. | 606/151 |
| 6,375,671 B1 | * 4/2002 | Kobayashi et al. | 606/213 |
| 6,485,504 B1 | * 11/2002 | Johnson et al. | 606/216 |

* cited by examiner

Primary Examiner—Linda C. M. Dvorak
Assistant Examiner—Kenneth G Schopfer
(74) Attorney, Agent, or Firm—Allen, Dyer, Doppelt, Milbrath & Gilchrist, P.A.

(57) ABSTRACT

A system for fixation of a soft tissue tear includes a flexible, generally helical fixation element biased to a predetermined pitch. A hollow, generally helical insertion element is dimensioned to admit at least a distal portion of the fixation element into a lumen thereof. The insertion element's pitch along a central portion is larger than that of the fixation element. The insertion element is insertable in a screwing motion across the soft tissue tear and is positionable with the central portion bridging the tear. The fixation element is insertable into the insertion element, and the insertion element is removable in a reverse screwing motion, leaving the fixation element positioned across the tear. The positioning of the central portion permits the fixation element to contract following removal of the insertion element to bring the two bridged sides of the tear together, permitting them to heal. An orthopedic system for stabilizing two sections of a bone in spaced-apart relation includes an elongated guide element and a coil element having a bore dimensioned for threading over the guide element. The coil element is biased in an outward direction for fixating two sections of bone in a desired spaced-apart orientation.

14 Claims, 11 Drawing Sheets

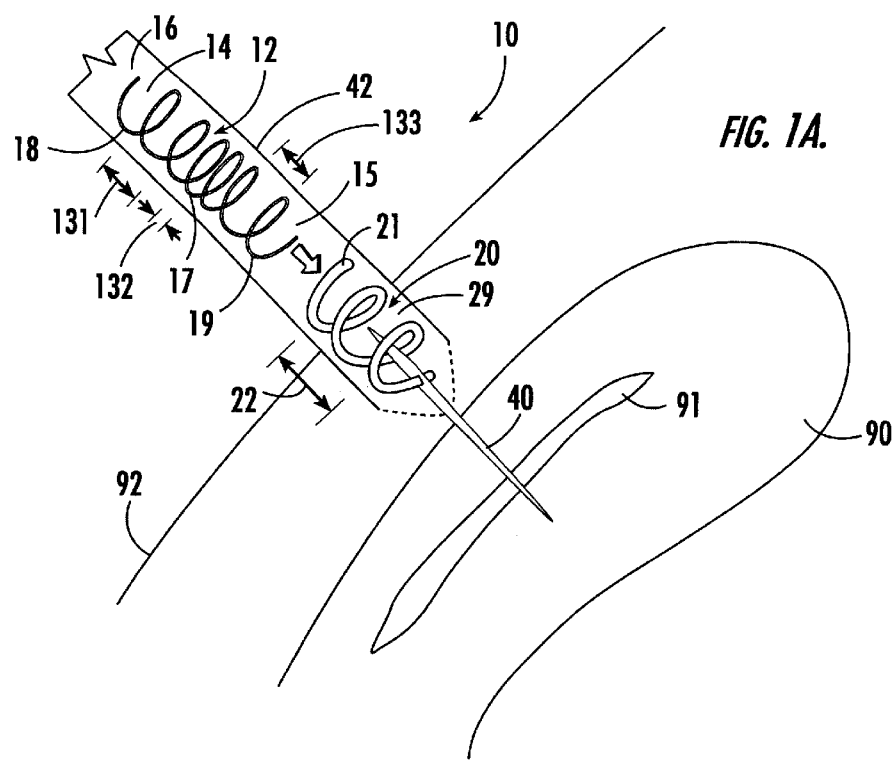
FIG. 1A.
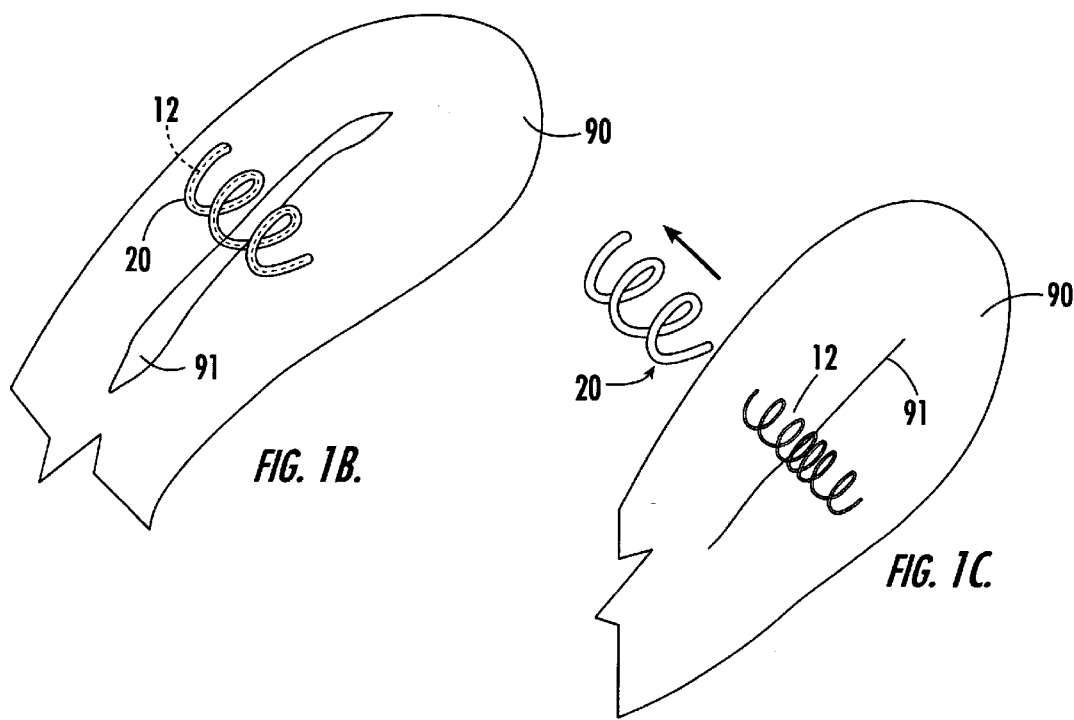
FIG. 1B.
FIG. 1C.

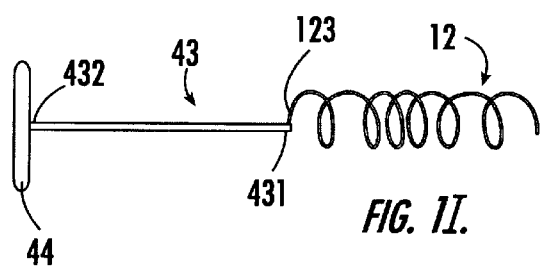
FIG. 1I.
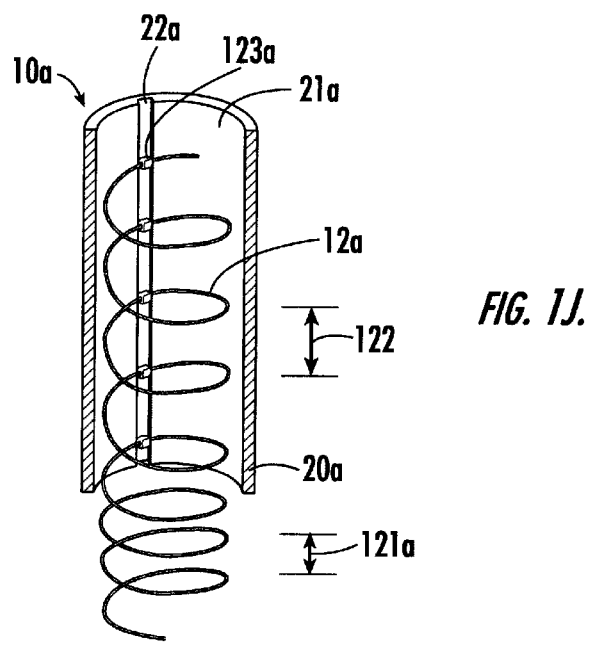
FIG. 1J.
FIG. 1K.
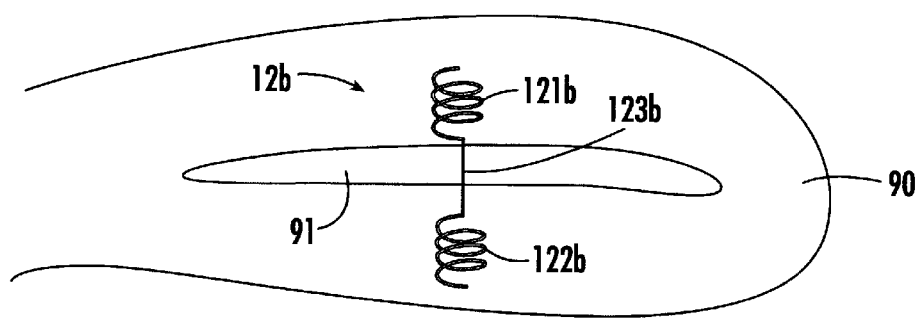

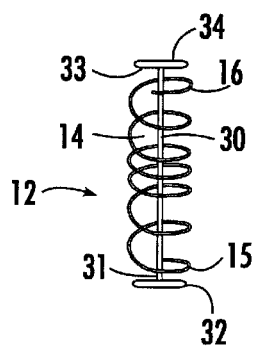
FIG. 2A.
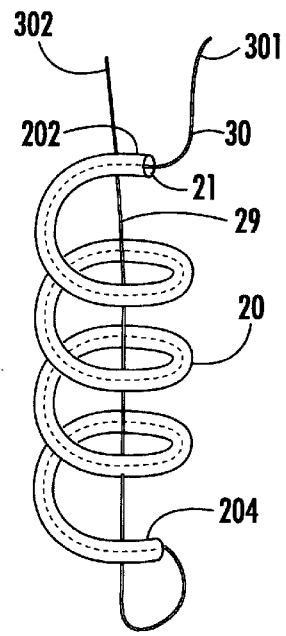
FIG. 2B.
FIG. 2C.
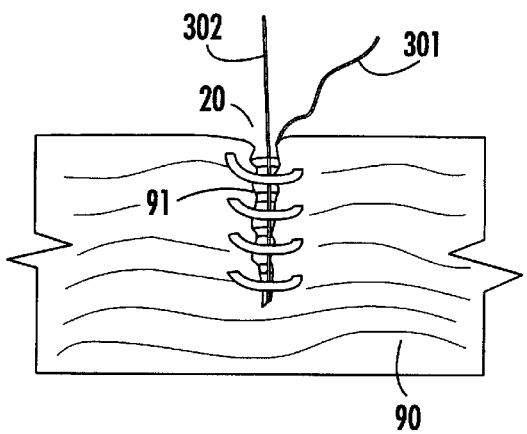
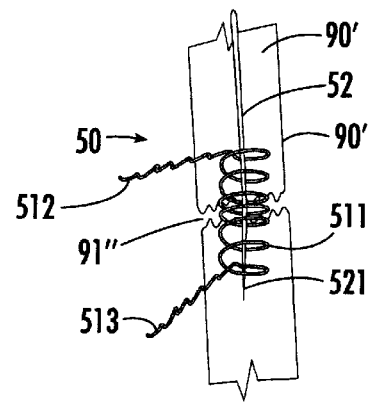
FIG. 2D.

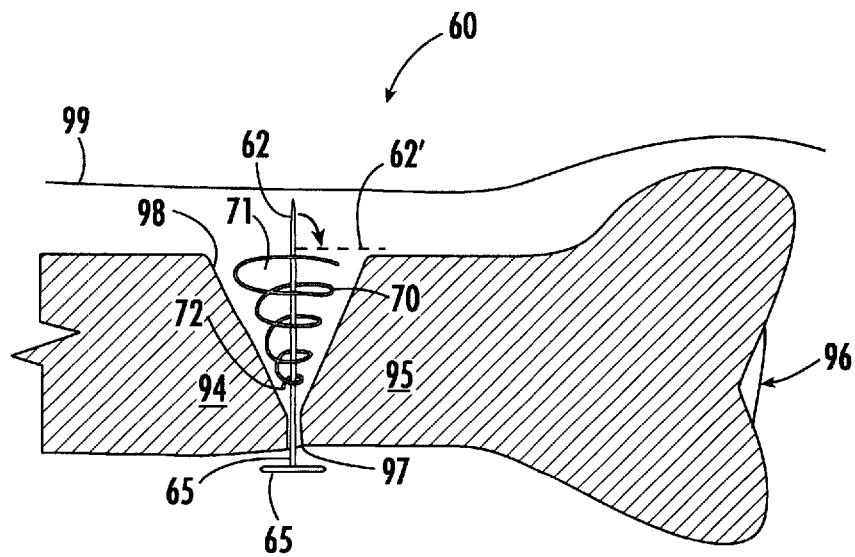
FIG. 5.
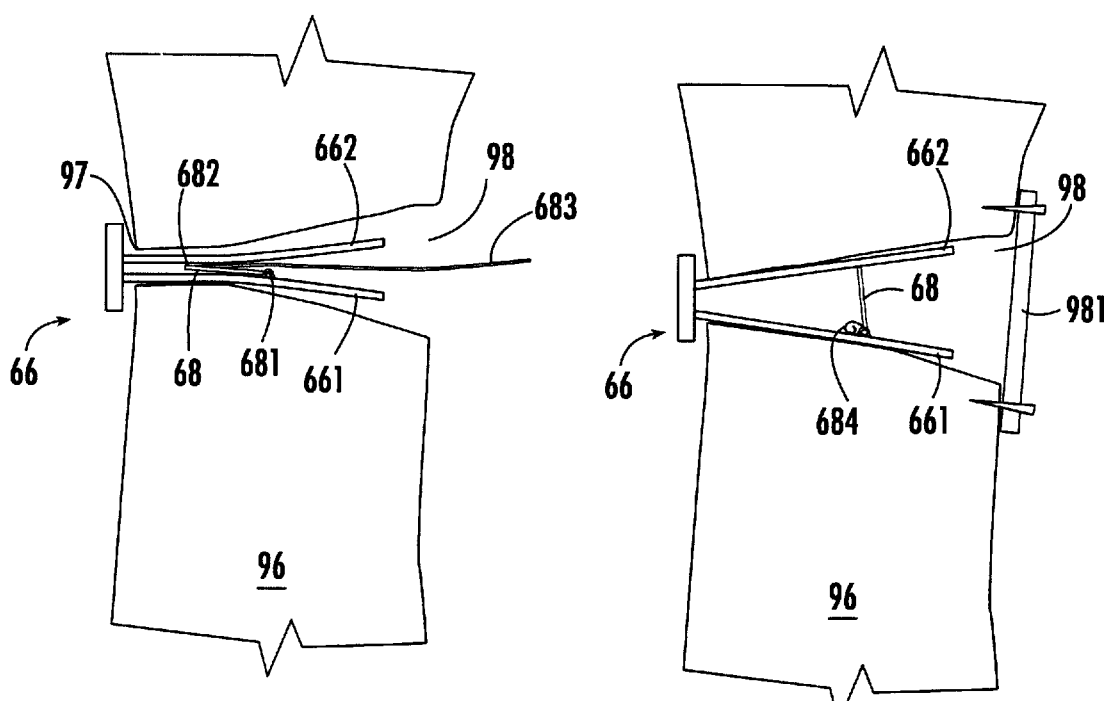
FIG. 6A.
FIG. 6B.

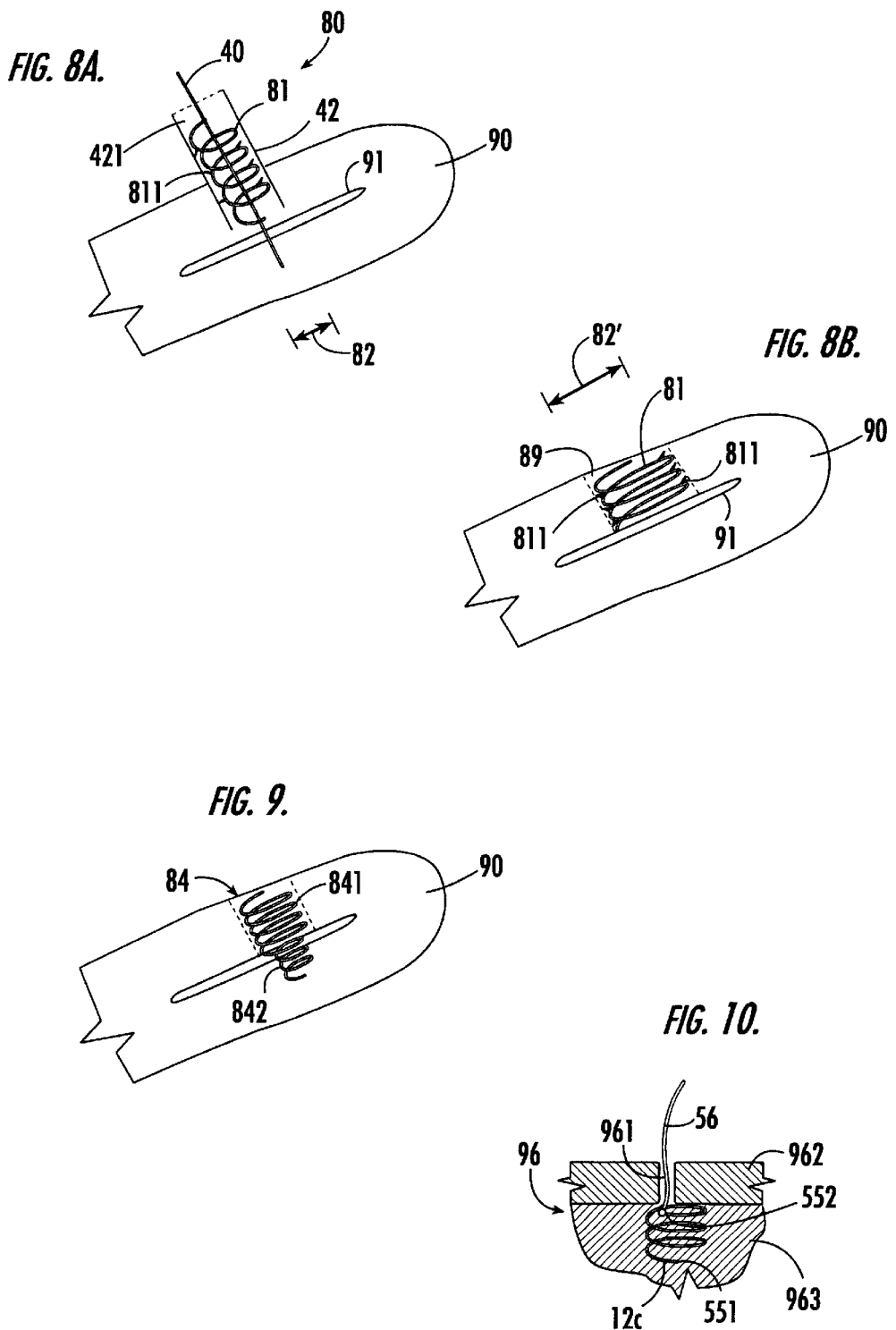

HELICAL ORTHOPEDIC FIXATION AND REDUCTION DEVICE, INSERTION SYSTEM, AND ASSOCIATED METHODS

BACKGROUND OF THE INVENTION

1. Field of the Invention

The present invention relates to surgical devices and methods, and, more particularly, to orthopedic devices and methods for fixating soft tissue and reducing fractures.

2. Description of Related Art

Orthopedic procedures are typically undertaken to repair structural injuries or address structural problems. Among these are fracture reduction and the fixation of soft tissue tears.

Soft tissue tears are often desired to be treated by placing the two sides of the tear into intimate (or tight) apposition to permit healing. This can be achieved, for example, by suturing the tear or by placing an implement into the tissue to breach the tear and bring the sides together.

A common soft tissue tear, especially in athletes, occurs in the menisci of the knee. Posterior peripheral tears of the menisci may be treated by an open technique, wherein sutures are placed along the tear. An arthroscopic technique may also comprise placing sutures along the tear or inserting a meniscal dart or screw of one of the types known in the art. Screws having heads, however, are known to cause problems within a joint, even if they are resorbable, since a typical resorption time is in the range of 6–9 months. Further, screws and darts are typically substantially rigid elements that can cause discomfort in the patient.

There are a number of fastener-type devices known in the art. A surgical fastener is disclosed by Screiber (U.S. Pat. No. 4,873,976) that comprises a shaft having at least one barb for locking the shaft in place when inserted into soft tissue. Bays et al. (U.S. Pat. Nos. 4,884,572 and 4,895,148) describe a surgical-repair tack and applicator and method of using them. The tack has a barb member and is made of biodegradable material having a degradation time selected to coincide with the healing time of the tissue. In an alternate embodiment, the tack's barb comprises a continuous helical barb.

A method and apparatus for repairing a meniscal tear is disclosed by Winters (U.S. Pat. No. 5,059,206), comprising a fastener having protrusions or barbs that is applied to a meniscal tear with a delivery device. Variable-pitch bioresorbable meniscal screws that are insertable across a tear are also taught by Justin and Winters (U.S. Pat. Nos. 5,569,252 and 5,730,744).

Another example of an orthopedic injury the treatment of which could be improved is a torn carpal ligament, which will permit the carpal bones to spread apart without securing them together during the healing process. At present this is addressed by connecting the affected bones with smooth pins, necessitating the immobilization of the wrist. These pins must then be removed after healing.

Yet another example of a fracture is the crushing of the distal aspect of the radial bone, which can leave a posterior defect after the reduction adjacent the bone's head. Such a fracture cannot be treated simply by applying a cast, since, left unattended, the wedgelike defect will permit the radius to deform upward to close the gap.

Current methods of treating such fractures include affixing plates to the bone, a procedure that is painful and may injure adjacent tendons; injecting paste into the defect zone, which does not consistently effect a correction and which cannot be modified once the paste sets; and inserting pins or external fixation, which can cause stress risers in the adjacent bone that can lead to stress fractures or loss of reduction from not directly supporting the bone defect.

SUMMARY OF THE INVENTION

It is therefore an object of the present invention to provide a device and method for reducing fractures.

It is a further object to provide such a device that biases the two sides of a wedge-shaped bone defect into a natural position to promote proper healing.

It is another object to provide such a device that does not impinge upon surrounding soft tissue.

It is an additional object to provide such a device that is insertable arthroscopically or percutaneously.

It is yet a further object to provide a device and method for fixating a soft tissue tear.

It is yet another object to provide such a device that brings two sides of a soft tissue tear into apposition to promote healing.

An additional object is to provide a device and method for compressing adjacent bones during the healing of a connecting ligament without excessive constraint and maintaining a desired physiological relationship.

A further object is to provide a device and method for promoting healing of a fixated soft tissue tear.

Another object is to provide a device and method for creating a vascular access channel.

These and other objects are achieved by the present invention, an orthopedic reduction and fixation device, insertion system, and associated methods. The system for fixation of a soft tissue tear comprises the device, which in one embodiment comprises a flexible, generally helical fixation element biased to a predetermined pitch. In an alternate embodiment the device comprises a helical portion and a nonhelical portion, the helical portion biased to a predetermined pitch. In yet another embodiment the helix is biased to a first pitch along a distal portion, a second pitch along a central portion, and a third pitch along a proximal portion. The second pitch is smaller than the first and the third pitches, so that, upon insertion across a tear, the central portion will contract, bringing the sides of the tear closer together to promote healing.

The system also includes a hollow, generally helical insertion element dimensioned to admit at least a distal portion of the fixation element into a lumen thereof. The insertion element in one embodiment has a first pitch along a distal portion, a second pitch along a central portion, and a third pitch along a proximal portion. The second pitch is larger than the first and the third pitches and is also larger than the fixation element predetermined pitch. The insertion element is further insertable in a screwing motion across the soft tissue tear and is positionable with the central portion bridging the tear.

The fixation element is insertable into the insertion element, and the insertion element is removable in a reverse screwing motion, leaving the fixation element positioned across the tear. The positioning of the central portion permits the fixation element to contract following removal of the insertion element to bring the two bridged sides of the tear together, permitting them to heal.

Among the many advantages of the helical fixation element is its dynamic nature; unlike a rigid or semirigid screw, a flexible helix can move with the tissue, accommodating stresses laterally and under compression and stretching, while returning to its natural predetermined pitch. Alternatively, in some embodiments the element may have a higher level of stiffness, particularly along the portion of the element bridging the tear, to resist stretching/elongation under physiological conditions. Additionally, since the device is headless, there can be no additional trauma caused by such a protrusion. Further, since a helical structure can be inserted into a hole only as large as the diameter of the coil element, the wound needed for insertion is far smaller than would be required for another type of anchoring element, such as a screw; the resistance to pullout is also much better, an axial force alone not being able to achieve removal. It is also believed that the helical device can effect greater compression than a screw. In addition, even if the coil breaks in the tissue, the complex fixation with the tissue enables a maintenance of structural integrity.

A further embodiment of the invention comprises suture material as a component of the fixation element. In a first subembodiment suture material resides within an insertion element lumen for insertion. Upon withdrawal of the insertion element the suture material remains, along a substantially helical pathway, essentially "stitching" the tear together. In a second subembodiment the fixation element comprises a nonresorbable suture material core surrounded by a resorbable, shape-retaining material formed into a substantially helical shape along at least a portion thereof adapted for placement across the tear. In use, then, when the fixation element is placed across the tear, the resorbable material preferably remains in place for a time commensurate with a healing time; following resorption, the suture material remains, providing permanently added stability.

Another embodiment of the invention comprises an orthopedic system for stabilizing two sections of a bone in spaced-apart relation, such as is desired in crushing-type injury to a wrist. The system includes an insertion guide that comprises an elongated guide element having a length sufficient to span a bone requiring fixation. The guide element also has a diameter that is dimensioned for insertion through a bore in the bone or through a fracture defect. The insertion guide also comprises means for preventing a distal end of the guide element from entering the bone bore. The preventing means may comprise a deployable element that is movable between an insertion orientation and an anchoring orientation wherein the guide element from entering the bone bore.

The system further includes a coil element that is dimensioned for insertion into a fracture or defect and has a bore dimensioned for threading over the guide element. The coil element is biased in an outward direction for fixating two sections of bone in a desired spaced-apart orientation.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIGS. 1A–1C is an exploded view of a first embodiment of the orthopedic fixation system with the device entering soft tissue having a tear (FIG. 1A); being positioned across a soft tissue tear inside the insertion device (FIG. 1B); and in place with the insertion device removed (FIG. 1C).

FIG. 1I is a side view of a combined device and introducer.

FIG. 1J is a cutaway view of another spiral device and introducer embodiment.

FIG. 1K illustrates the use of a hybrid coil/suture device used in meniscal repair.

FIG. 2A is a perspective view of the system of FIG. 1A with a limiting element in place.

FIG. 2B is a side perspective view of an alternate embodiment of the fixation system of FIG. 1A for use in repairing soft tissue tears.

FIG. 2C is a top plan view of the embodiment of FIG. 2B in place in soft tissue in repairing a tear therein.

FIG. 2D is a side view of a hybrid coil and suture fixation device.

FIG. 5 is a side perspective view of a third embodiment of the orthopedic fixation device being deployed to reduce a distal radial fracture.

FIGS. 6A and 6B are side perspective views of a fourth embodiment in an insertion position (FIG. 6A) and being deployed for fixating a tibial fracture (FIG. 6B).

FIGS. 8A and 8B are side cross-sectional views of a fifth embodiment of the fixation device adapted for creating a vascular access channel in the insertion position (FIG. 8A) and in the expanded position (FIG. 8B).

FIG. 9 is a side cross-sectional view of a sixth embodiment of the fixation device adapted to differentially create a vascular access channel as well as fixate a soft tissue tear.

FIG. 10 illustrates the use of a spiral device as a suture anchor.

DETAILED DESCRIPTION OF THE PREFERRED EMBODIMENTS

Figure 1D:
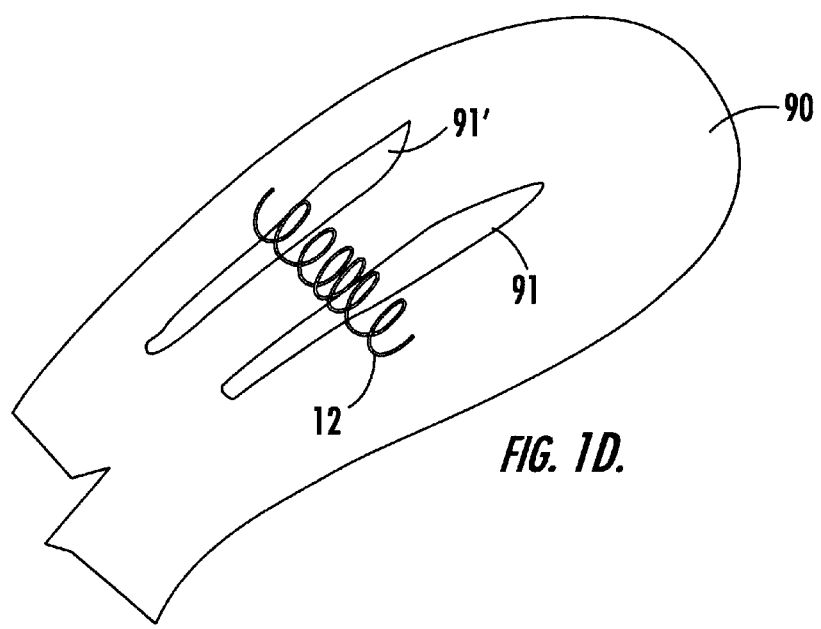
FIG. 1D is a perspective view of the embodiment of FIG. 1A being used to fixate a double tear in soft tissue.
Figure 1E:
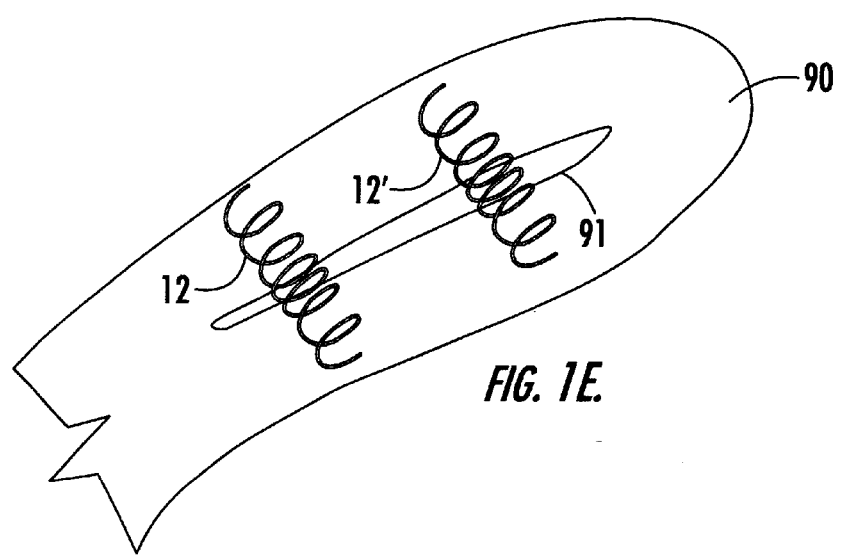
FIG. 1E is a perspective view of a plurality of devices of FIG. 1A being used to fixate a soft tissue tear.
Figure 1F:
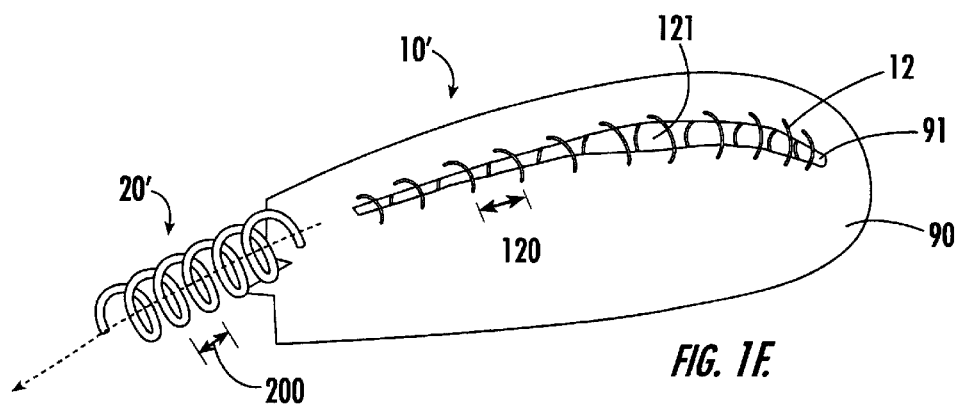
FIG. 1F is a perspective view of a helical device as in FIG. 1A having been positioned along a curved soft tissue tear with a curved insertion device.
Figure 1G:
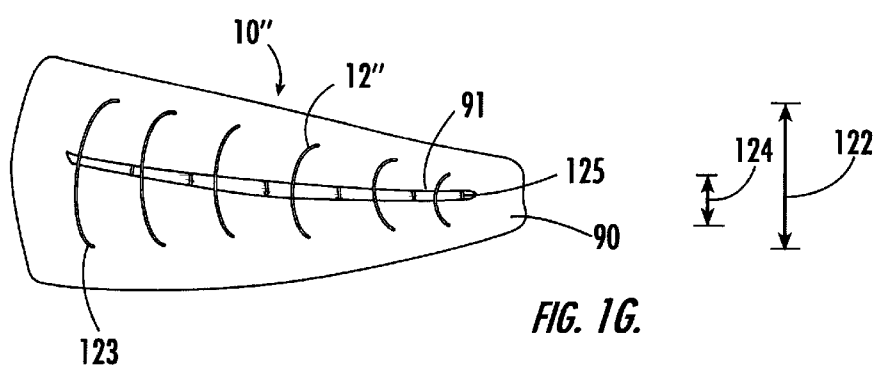
FIG. 1G is a side view of a wedge-shaped helical device in position in a meniscus.
Figure 1H:
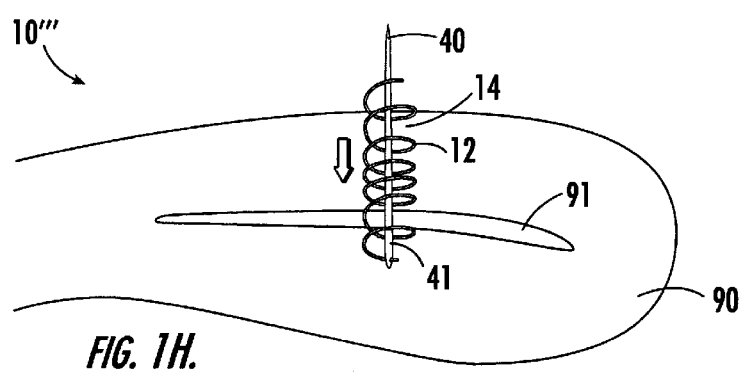
FIG. 1H is a perspective view of the device being introduced into soft tissue over a needle without an insertion element.
Figure 1L:
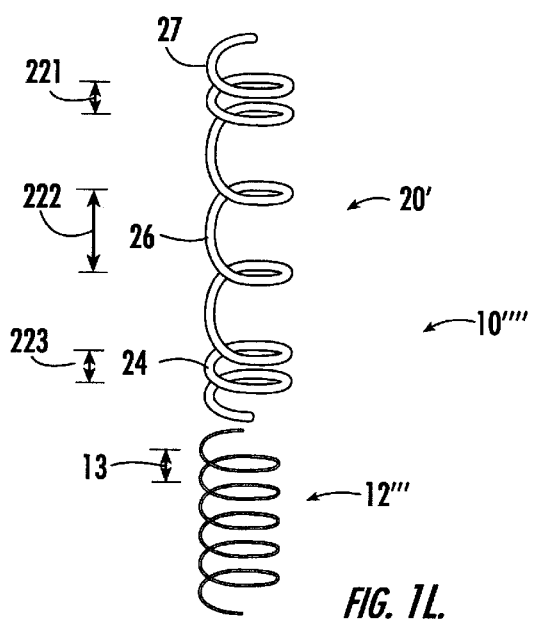
FIG. 1L is an exploded view of a helical device and insertion element, with the insertion element having a variable pitch.
Figure 1M:
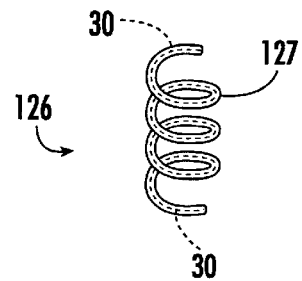
FIG. 1M is a perspective view of a fixation element having a bioresorbable overlayer and a flexible core.
Figure 1N:
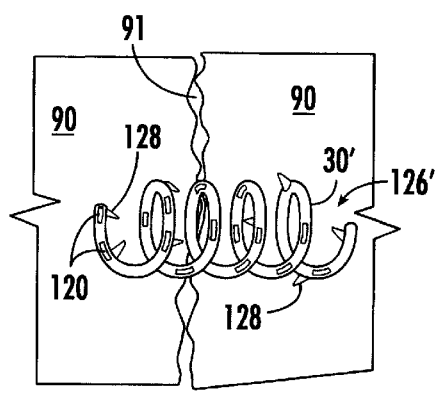
FIG. 1N illustrates a flexible core having surface barbs left in place across a tear.
Figure 1O:
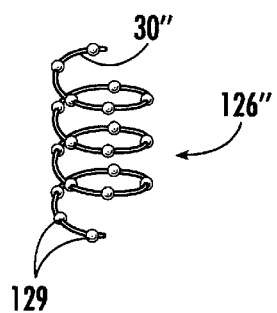
FIG. 1O illustrates a flexible core having surface beads.

A description of the preferred embodiments of the present invention will now be presented with reference to FIGS. 1A–1O.

Several embodiments of the present invention will be presented. As indicated above, it is desirable to provide a reducing and fixation system for addressing a plurality of orthopedic problems.

Systems for Fixation of a Soft Tissue Tear

A first embodiment of the present system is an orthopedic system 10 for fixation of a soft tissue 90 tear 91 (FIG. 1A), here shown as a meniscal tear, although this is not intended as a limitation. The system 10 comprises a flexible, generally helical fixation element 12 that is biased to a predetermined pitch, preferably a plurality of pitches along a length thereof. The helical element 12 has a central lumen 14 extending between a distal end 15 and a proximal end 16. In a preferred embodiment a central portion 17 of the helix 12 has a higher spring constant than the end portions 18,19. In this embodiment the helix 12 has a first pitch 131 along the proximal end portion 18, a second pitch 132 along the central portion 17, and a third pitch 133 along the distal end portion 19, wherein the second pitch 132 is smaller than the first 131 and the third 133 pitches. The helix 12 may also be bioresorbable and comprise a material known in the art having a resorption constant commensurate with a healing time of the soft tissue tear 91 to be repaired.

The system 10 further comprises a hollow, generally helical insertion element 20 that has a central axial lumen 29 and a helical lumen 21 dimensioned to admit at least a distal portion of the helix 12 thereinto. The insertion element 20 has a substantially constant pitch 22 along a length thereof.

In an alternate embodiment (FIG. 1L) the fixation element 12''' has a substantially constant pitch 13 therealong, but the insertion element 20' has a variable pitch. Here the insertion element 20' has a first pitch 221 along a proximal portion 27, a second pitch 222 along a central portion 26, and a third pitch 223 along a distal portion 24, with the second pitch 222 greater than the first 221 and the third 223. This configuration similarly causes the helix 12''' to contract the tear sides together when in place thereacross.

In another embodiment (FIG. 1M) the fixation element 126 comprises a suture material 30 core surrounded by a resorbable, substantially shape-retaining helical overlayer 127. In use this embodiment is positioned as those described above, but following insertion the resorbable overlayer 127 bioresorbs over time, preferably over a time commensurate with the healing time of the tear, leaving the suture core 30 in place essentially permanently, to continue to provide support in the region of the tear but without the presence of a rigid member. This embodiment is envisioned as useful, for example, with partially healed meniscal tears under the surface, with the suture 30 having less chance of forming a cyst as with previously known devices.

In two related embodiments the fixation element 126', 126'' comprising suture material 30',30'' has directional barbs 128 (FIG. 1N) or beads 129 (FIG.1O), respectively. The barbs 128 are preferably pointed toward a central region so that they are pointing toward the tear when in place thereacross. These surface protrusions 128,129 are released when the overlayer 127 bioresorbs, and achieve improved purchase into the tissue.

The embodiment of FIG. 1N additionally has a plurality of fenestrations 120 therein. These fenestrations 120 provide a porous surface into which fibrous tissue may invaginate, again achieving an improved purchase to and retention within the tissue.

The insertion element 20 is insertable in a screwing motion across the soft tissue tear 91 and is positionable with the central portion 25 bridging the tear 91 (FIG. 1B). The fixation element 12 is insertable into the insertion element's lumen 21, and the insertion element 20 is removable in a reverse screwing motion, permitting the fixation element 12 to be left in position across the tear 91 (FIG. 1C). Once the insertion element 20 is removed, at least the central portion 17 of the helix 12 contracts to its natural, predetermined pitch 13 to bring two sides of the tear 91 together with compression. This apposition of the tear's sides will permit healing to occur.

In a preferred embodiment the system 10 further comprises means for limiting the helix 12 to a predetermined maximum length but does not limit compression to a smaller length. Such a limiting means may comprise, for example, a flexible limiting element, such as a piece of suture 30, having a first end 31 positioned in restraining relation to the distal end 15 of the helix 12. This may be accomplished, in a particular embodiment, by the suture's first end 31 comprising a "T"-shaped element having a crosspiece 32 flexibly attached to the suture 30. The crosspiece 32 is then insertable through the helix's lumen 14 and braceable against the helix's distal end 15, not unlike the attachment pieces used to affix clothing tags.

Figure 2E:
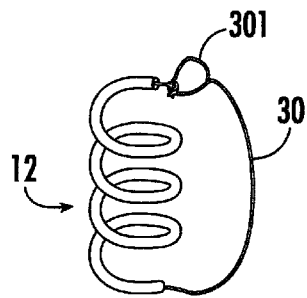
FIG. 2E is a side view of a helical fixation device with a limiting length of suture and suture loop.

Means are also positioned at a second end 33 for preventing the helix's proximal end 16 from passing therebeyond. Again this means may comprise a "T"-shaped element at the second end 33, a crosspiece 34 thereof positionable across the helix's proximal end 16 (FIG. 2A).

This embodiment of a limiting element is not intended to represent a limitation on the invention, as one of skill in the art will recognize numerous possible variations thereto. For example, a "bead" at one end can also be used to retain that end in a desired position. Alternatively (FIG. 2E), a loop 301 of flexible material such as suture 30 may be affixed to one end of the helix 12 that can be affixed following or during fixation of the tear 91 to the other end to provide additional stability and length limiting of the helix 12.

In another embodiment of this system for repairing soft tissue 90 tears 91, a helical insertion element 20 as described above is loaded with a piece of highly flexible material, for example, but not limited to, suture 30 (FIG. 2B). This flexible material for this embodiment is preferably not biased to a particular orientation. The suture 30 is passed through the lumen 21, with a first end 301 emerging from the insertion element's proximal end 202. A second end 302 of the suture 30 emerges from the insertion element's distal end 204, and then is passed through the axial lumen 29, so that the second end 302 and the first end 301 are both accessible proximal of the insertion device 20. Preferably the distal end 204 of the insertion element 20 is pointed for penetrating the soft tissue 90.

In use, the loaded insertion element 20 is inserted in spiral fashion to "stitch" two opposing sides of the tear 91 together (FIG. 2C). Then the insertion element 20 is removed from the soft tissue 90, leaving the suture 30 in place. Finally, the suture 30 is tightened by pulling the ends 301,302 to a desired tightness and knotting them, which leaves a tear 91 with closely opposed sides that can 20 more readily heal than those repaired with other methods known in the art. The suture 30 may be of the resorbable or nonresorbable type depending upon the type and site of the tear.

Another hybrid type of system 50 comprises a fixation element 51 that includes a helical central portion 511. This helical portion 511 should have sufficient stiffness to fixate a soft tissue tear 91". The element 51 further includes two elongated flexible elements 512,513, one affixed to each end of the helical portion 511. A preferred embodiment of the system 50 further includes a narrow elongated element 52.

In use, the elongated element 52, typically having a pointed tip 521, is inserted across a tear 91", shown in FIG. 2D as a ruptured tendon 90'. In this case the tendon ends are aligned axially first. The helical portion 511 is then screwingly inserted over the elongated element 52 in bridging relation to the tear 91", and the elongated element 52 is removed. Next the flexible elements 512,513, which may comprise, for example, lengths of suture material, are pulled outside the tissue 90' and secured, such as by knotting. A particular advantage of this system is that frayed ends of the tendon 90' may be captured and held by the helical portion 511, while leaving a substantial amount of the tissue exposed and available for fluid contact.

The system of the present invention in a preferred embodiment also comprises a guide needle 40. The needle 40 has a diameter that is smaller than the axial bore 29 of the insertion element 20 and is insertable across the tear 91. The needle 40 is also sufficiently long to enter the tissue 90 and bridge the tear 91 (FIG. 1A).

The insertion element 20 is insertable across the tear 91 in encompassing relation to the needle 40. In certain embodiments the guide needle 40 may be shaped to optimize access to the tear 91. For example, in repairing a knee meniscus, the needle 40 would preferably be curved in order to permit access around adjacent bone structure.

The system 10 further comprises a cannula 42 adapted to pierce a skin 92 of a patient and into the soft tissue 90 proximal of the tear 91 (FIG. 1A). The cannula 42 is adapted to admit the insertion element 20 therethrough for positioning across the tear 91.

Figure 3:
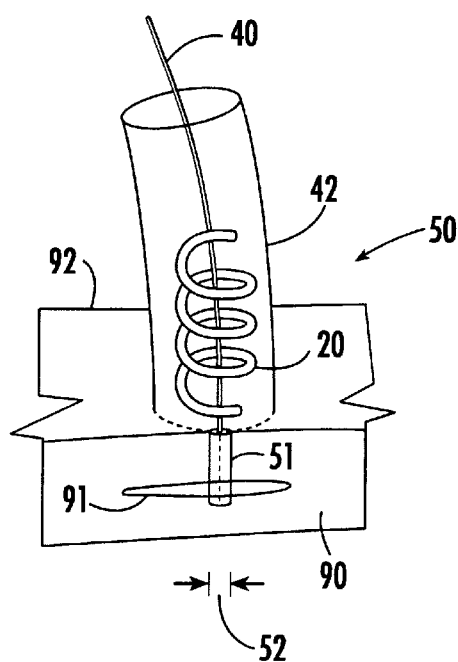
FIG. 3 is an exploded view of a second embodiment of the orthopedic fixation system with a tissue dilator in an insertion position.
Figure 4:
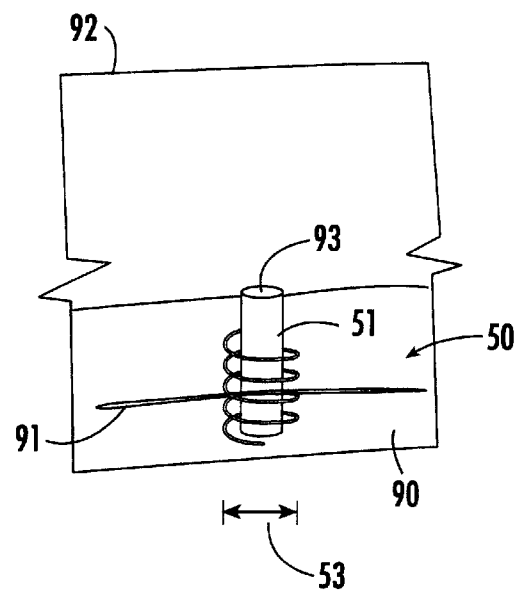
FIG. 4 illustrates the embodiment of FIG. 3 with the dilator in an expanded position.

In a particular embodiment the system 50 (FIGS. 3 and 4) may also comprise means for dilating a hole 93 in the soft tissue 90. The dilator 51, a generally cylindrical element, is movable between an insertion position having a first diameter 52 that is adapted to slide within the cannula 42 and over the guide needle 40 and a dilating position having a second diameter 53 that is larger than the first diameter 52. The dilating position is for maintaining a hole 93 that facilitates the healing of the tear 91, by permitting the invasion of reparative tissue. The second diameter 53 should be sufficiently small to admit the insertion element 20 thereover. Alternatively, means may be provided for inserting a fibrin clot 94 into the hole 93 for further facilitating healing of the tear 91.

The method of fixating a soft tissue tear 91 with the system 10 as described above comprises the steps of inserting a cannula 42 through the skin 93 into the soft tissue 90 (FIG. 1A). Then a guide needle 40 is inserted across the tear 91 and the insertion element 20, over the needle 40 across the tear 91 in a screwing motion. Next at least a distal portion of the helix 12 is inserted into the insertion element's lumen 21, which may be accomplished from either direction. Finally, the insertion element 20 is withdrawn in an unscrewing motion (FIG. 1B), leaving the helix 12 in position across the tear 91 (FIG. 1C). The central portion 17 of the helix 12, upon withdrawal of the insertion element 20, contracts to its predetermined pitch 13, which draws two sides of the tear 91 together and permits the tear 91 to knit.

It may also be seen that the device 12 may be used to repair double tears 91,91' in a soft tissue 90 by advancing one device 12 across both tears 91,91'(FIG. 1D) to achieve fixation thereof.

Further, a plurality of helical devices 12 may be used to repair a unitary tear 91 (FIG. 1E).

For example, a first device 12 could be positioned along the tear 91 in one location and a second device 12', across the tear 91 in another location.

In yet another embodiment of the system 10', a helical fixation element 12 is positioned along the axis of a tear 91 with an insertion element 20' shaped to conform with the shape of the tear 91. In the so-called "bucket handle" tear 91 of a meniscus 90 shown in FIG. 1F, which typically will not heal easily, the insertion element 20' has an arcuate curvature adapted to proceed along the tear 91, Upon its removal, the helix 12 remains in place, bridging the tear with multiple points of fixation. Preferably the insertion element 20' has a pitch 200 greater than a pitch 120 to which the helix 12 is biased, so that the helical lumen 121 decreases upon removal of the insertion element 20'. The repair of this tear 91 permits the adjacent condyle to become a compressive rather than disruptive load.

In yet another embodiment of the system 10"(FIG. 1G) the helical fixation element 12" is generally wedge-shaped for fixation of a tear 91 in a wedge-shaped portion of tissue, such as, but not limited to, a meniscus 90. That is, the helix 12" has a first diameter 122 at a proximal end 123 that is larger than that 124 at a distal end 125. Likewise, the insertion element (not shown) would have a first diameter at a proximal end that is larger than that at a distal end.

In use, the helix 12" is inserted into the insertion element, which is screwed either across or along a tear 91. Next the insertion element is removed, leaving the helix 12" in place. A particular advantage of the helical shape in this embodiment lies in the fact that a larger-diameter device can be introduced into the tissue without causing the damage that would ensue if a screw of the same diameter were to be inserted.

In addition, it can be appreciated by one of skill in the art that the embodiments of the present invention, such as those illustrated in FIGS. 1F and 1G, are easily accommodated to particular situations, and a variety of shapes of helical and insertion elements could easily be provided to optimize the desired repair.

Another system 10'" for fixating a soft tissue tear 91 comprises a needle 40 that has a pointed distal tip 41 (FIG. 1H). In use, the needle 40 is inserted into the tissue 90 in bridging relation to the tear 91, and the helix 12 is inserted into the soft tissue 90 in a screwing motion with the lumen 14 of the helix 12 in surrounding relation to the needle 40. Once the helix 12 is positioned as desired, the needle is withdrawn, leaving the helix 12 in bridging relation to the tear 91. This system 10'" is contemplated for use without an insertion element, such as directly through the patient's skin into the tear site. For this embodiment the helix 12 has sufficient structural integrity on its own to permit such an insertion, and may comprise a stiffer material such as a metal.

The helix 12 in this embodiment can be presized to a desired situation; alternatively, the helix 12 could be frangible or cuttable to a desired length either before or after insertion.

Figure 1P:
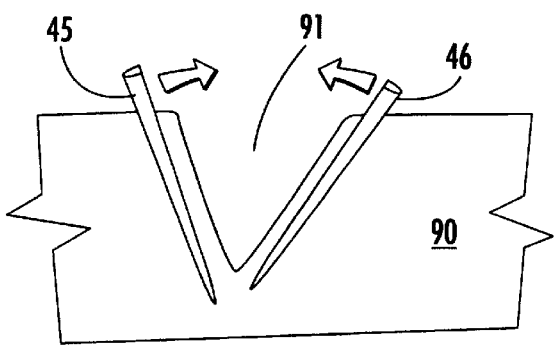
FIGS. 1P–1R illustrate a system and method for fixating a tear using wires for closing the tear (FIGS. 1P, side cross section, and 1Q, top plan view) and a helical fixation element for fixating the tear (FIG. 1R).
Figure 1Q:
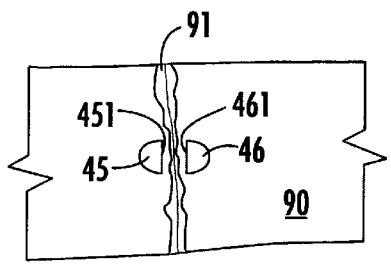

In yet another embodiment a pair of wires 45,46 are inserted on opposite sides of a tear 91 that extends through to a surface of a tissue 90, wherein the tear 91 will typically spread apart into a "V"-shaped cross section (FIG. 1P). The wires 45,46 are then drawn together at their proximal ends 452,462. Preferably the wires 45,46 have facing surfaces 451,461 that are substantially planar, so that upon drawing them together they abut smoothly (FIG. 1Q).

Figure 1R:
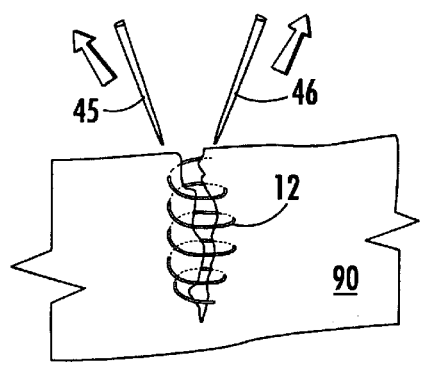

Next the helix 12 is advanced down the coupled wires 45,46, and then the wires 45,46 are removed from the tear, leaving the helix 12 in place stabilizing the tear 91 (FIG. 1R).

In a related system the helix 12 is frangibly attached at a proximal end 123 to the distal end 431 of an insertion device 43, a generally linear elongated wire having a handle 44 at the proximal end 432 (FIG. 1I). In use, the handle 44 facilitates the screwing motion to insert the helix 12. Once a tear is bridged, the insertion device 43 is broken away, leaving the helix 12 in place at the desired site.

In FIG. 1J is illustrated another embodiment of a fixation system 10a, wherein the helical fixation element 12a is movable between a first orientation having a first pitch 121a and a second orientation having a second pitch 122. The helical element 12a is biased to the first pitch 121a, and has a plurality of laterally extending protrusions 123a affixed thereto. The protrusions 123a are axially alignable in the second orientation.

A generally cylindrical insertion element 20a is dimensioned to admit at least a distal portion of the fixation element 12a into a lumen 21a thereof. The insertion element 20a has a groove 22a that extends longitudinally within the lumen 21a that is adapted to admit the protrusions 123a thereinto in longitudinal alignment. This serves to retain the helical element 12a in the second orientation.

Another system and method for fixating a soft tissue tear includes a fixation element 12b that comprises a first 121b and a second 122b helical fixation section (FIG. 1K). A section of substantially constant-length material, such as suture material 123b, is affixed to an end of each of the helical fixation sections 121b,122b. In use, the first helical fixation section 121b is inserted into a piece of soft tissue 90 on a first side of a tear 91 therein. Next the second helical fixation section 122b is inserted into the piece of soft tissue 90 on a second side of the tear 91 sufficiently far that the material 123b is substantially taut across the tear 91. The material 123b may or may not be flexible depending upon the situation.

Systems for Reduction of a Bone Fracture

This embodiment of the invention is an orthopedic system 60 for stabilizing two sections 94,95 of a bone 96 in spaced-apart relation. The system 60 comprises an insertion guide that comprises an elongated guide element 61, which has a length that is sufficient to span the bone 96 requiring fixation and a diameter that is dimensioned for insertion through a bore 97 in the bone 96.

The system 60 further comprises a coil element 70 that is dimensioned for insertion into a fracture 98 and having an axial lumen 71 dimensioned for threading over the guide element 61. The coil element 70 is biased in an outward direction for fixating two sections 94,95 of bone 96 in a desired spaced-apart orientation. Preferably the coil element 70 has a pointed distal end 72 adapted for insertion through the patient's skin 99. The coil element 70, as above, may if desired comprise a bioresorbable material.

It is also preferred that the guide 61 further comprise means for retaining the coil element 70 to a desired maximum length. Such a retaining means may comprise, for example, the guide's proximal portion 62 being bendable from a substantially linear insertion position to a retaining position 62' generally perpendicular to the coil element's lumen 71.

The insertion guide 61 also comprises means for preventing a distal end 65 of the guide element 62 from entering the bone bore 97. In a particular embodiment the preventing means comprises a pin 65 that is rotatably affixed to the guide 61 and is movable between an insertion position substantially parallel to the guide 61 and a deployed position substantially normal to the guide 61 for bracing against the bone 96 surface.

A particular embodiment is contemplated for a situation in which the fracture region 98 is smaller in a distal portion than in a proximal portion. For this instance, the coil element 70 comprises a generally wedge-shaped helical spring. In this embodiment the user selects a wedge size appropriate for achieving sufficient engagement with the cortex. Depending upon the shape of the fracture region, the coil element 70 could be cylindrical or ovoid in order to optimally fit the internal contour of the distal radius for cortical contact.

In a particular embodiment it is also advisable to inject a bone-forming (osteoinductive) material into the coil element 70 in place in the fracture region 98 to stimulate healing.

Figure 6C:
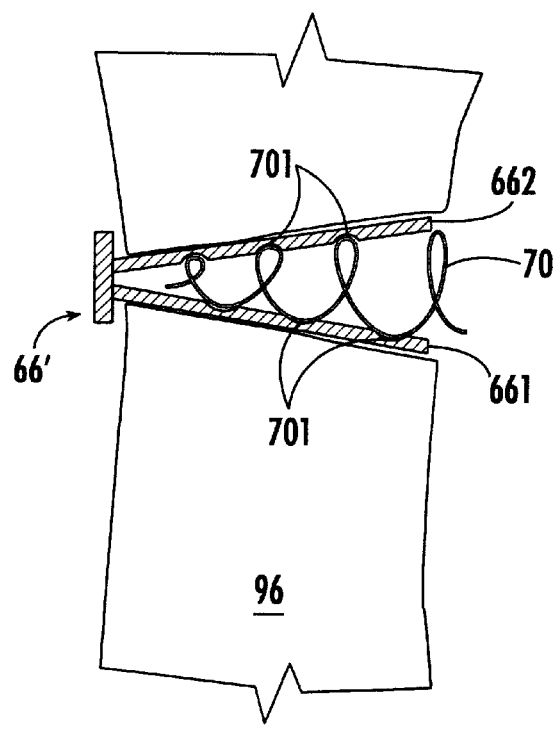
FIG. 6C is a side perspective view of a tibial fracture being stabilized with a pair of arms and a helical element.

In another embodiment, a device 66 for stabilizing two sections of fractured bone 96, such as a tibia, eliminates the need for an external fixator as is currently known in the art, which is believed to reduce complications during healing such as infections and irritation. This device 66 comprises a pair of arms 661,662, hingedly connected together at a first end to a stop 68 that is dimensioned to prevent its movement into a bore 97 at the smaller end of the fracture 98. A stop 68 is hingedly connected at a first end 681 along a central portion of a first arm 661 for movement between an insertion position (FIG. 6A) with the second end 682 adjacent the first arm 661 wherein the arms 661,662 are closely opposed and a deployed position (FIG. 6B) wherein the arms 661,662 are splayed apart at their second ends, the second end 682 of the stop 68 bracing the second arm 662 and substantially perpendicular to both arms 661,662.

Means are provided for moving the stop 68 to the deployed position. A first moving means comprises a flexible member such as suture 683 affixed adjacent the stop's second end 682 that can be pulled by the user to move the stop 68 to the deployed position (FIG. 6A). A second moving means comprises a spring 684 affixed to the first arm 661 in biasing relation to the stop 68 for biasing the stop 68 to the deployed position (FIG. 6B).

In order to improve the fixation, a plate 981 may be affixed to the bone surface adjacent the wider end of the fracture 98.

For additional support, a pair of devices 66 may be positioned within the fracture 98 in generally perpendicular relation to each other.

In an alternate, related embodiment 66' a helical element 70 is insertable into the fracture between the arms 661,662 (FIG. 6C) to stabilize the fixation. In a preferred embodiment "skids," or groove means, 701 are provided along the inner surfaces of the arms 661,662 to guide the helix 70 into the gap.

System for Stabilizing Opposing Articular Bone Surfaces

Figure 7:
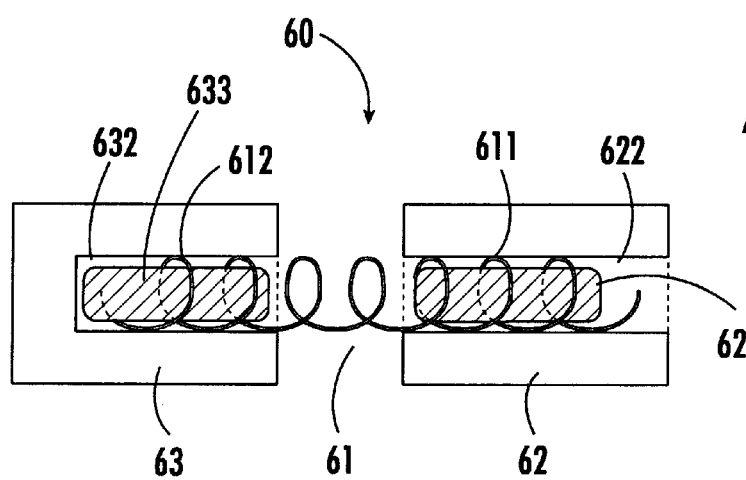
FIG. 7 is a side perspective view of a fourth embodiment of the orthopedic fixation device for use in opposing articular bone surfaces.

This embodiment of a system 60 (FIG. 7) is for use in situations in which it is desired to retain a pair of bones 62,63 in a predetermined orientation relative to one another. For example, in the case of carpal ligament damage, a pair of carpal bones 62,63 could splay apart into unphysiological positions and inhibit ligament healing. This can occur, for example, when the ligament between the scaphoid and lunate is damaged, permitting the capitate to advance therebetween and deform the hand.

The system 60 of the present invention for addressing this situation comprises a device 61 having a first 611 and a second 612 end portion and a central helical portion 613 having a spring constant adapted to retain the bones 62,63 in the desired orientation. The first 611 and the second 612 end portions are adapted for insertion into and retention within bone tunnels 622,632.

In a particular embodiment of this system 60, a generally coaxial bore 622,632 is created through the bone 62 and into bone 63. The first end portion 611 of the device 61, here shown as helical, is positioned within the bore 622, and the second end portion 612, also helical, within the bore 632. Means are provided for retaining the end portions 611,612 within the respective bores 622,632, such as screws 623,633 advanceable within the bores 622,632 to press the end portions 611,612 against the bores' walls. When thus retained, the central portion 613 biases the bones 62,63 into a desired orientation while at the same time permitting some flexibility during the healing process.

It may also be contemplated by one of skill in the art that additional embodiments could be envisaged, such as, but not limited to, end portions comprising press-fittable plugs.

System for Creating a Vascular Access Channel

The present invention also includes a system 80 for creating a vascular access channel 89 in soft tissue 90 adjacent a tear 91 to promote healing. The system 80 comprises a guide needle 40 that is adapted for insertion into soft tissue 90 adjacent a tear 91 therein. A cannula 42 is adapted for insertion into the soft tissue 90 in surrounding relation to the guide needle 40.

A generally helical element 81 has a diameter that is adjustable between an insertion diameter 82, which is dimensioned for insertion within the lumen 421 of the cannula 42 and in surrounding relation to the guide needle 40 (FIG. 8A) and an expanded diameter 82' greater than the insertion diameter 82 (FIG. 8B). The helical element 81 is biased to the expanded diameter 82'.

In a preferred embodiment the helical element 81 also has a plurality of generally outwardly-extending barbs 811 that are adapted to engage soft tissue 90 and enhance the channel-creating aspect of the device.

The benefit of such a system 80 is in improved healing, since the channel 89 created in the soft tissue 90 permits reparative tissue to invade, such as blood vessels and blood components. In addition, the channel 89 permits the insertion of a fibrin clot, also to enhance healing. In the meniscus of the knee, for example, only the outer 2–3 mm is vascularized, whereas the inner portion is less vascularized, making healing difficult. Present devices not only do not help in this process; they actively prevent reparative tissue entry, since they are typically solid devices. The helical element 81 of the present invention, however, creates a channel 89 while enabling access into the lumen thereof not only from the proximal end, but also from the sides.

The flexibility and adaptability of the device may also be seen in a dual use, wherein another embodiment of the helix 84 has differential spring constants along different portions thereof for different purposes. As shown in FIG. 9, a first portion 841 is biased to an expanded diameter for creating a channel 89 in the soft tissue 90, and a second portion 842 is biased to contract across the soft tissue tear 91 to contract the sides of the tear into apposition for healing.

System for Affixing a Flexible Element to a Bone

A system and method for fixating an element to a bone 96 are also provided within the scope of the present invention. A device 55 is provided that comprises a helical fixation element 12c that is insertable within a bone 96, either through a small hole 961 therein, or having a pointed distal end 551 and sufficient stiffness to pierce the bone surface itself to form the hole 961 (FIG. 10). The distal end 551 is continued to be inserted until the cortex 962 is passed through and the cancellous area 963 is reached. The device 55 further comprises means for affixing a flexible element 56 thereto at a proximal end 552.

Among the possible embodiments of this system and method are included a fixation of suture or a piece of soft tissue to the bone 96. As with the soft tissue embodiments above, the spiral nature of the fixation element creates a resistance to pullout while also providing excellent fixation characteristics. A much smaller hole is required to insert the helix than would be required for a screw of the same diameter, which means that less damage is being done to the bone structure.

It may be appreciated by one skilled in the art that additional embodiments may be contemplated, including alternately shaped coil elements and insertion elements for different applications.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. An orthopedic system for fixation of a soft tissue tear comprising:

a generally helical fixation element; and a hollow, generally helical insertion element dimensioned to admit at least a distal portion of the fixation element into a lumen thereof, the insertion element insertable in a screwing motion across the soft tissue tear and positionable with a portion between a distal end and a proximal end bridging the tear, the insertion element removable in a reverse screwing motion, leaving the fixation element positioned in bridging relation across the tear;

a guide needle having a diameter smaller than a bore of the insertion element and insertable across a soft tissue tear, the insertion element insertable across the tear in encompassing relation to the needle.

2. The system recited in claim 1, further comprising a cannula adapted to pierce a skin of a patient and into the soft tissue proximal of the tear, the cannula adapted to admit the insertion element and the guide needle therethrough for positioning across the tear.

3. The system recited in claim 1, wherein the fixation element is biased to a predetermined pitch and wherein the insertion element has a first pitch along a distal portion, a second pitch along a central portion, and a third pitch along a proximal portion, the second pitch larger than the first and the third pitches and than the fixation element pitch, wherein upon removal thereof the fixation element contracts along a central portion to bring two sides of the tear into closer apposition.

4. An orthopedic system for fixation of a soft tissue tear comprising:
   a generally helical fixation element;
   a hollow generally helical insertion element dimensioned to admit at least a distal portion of the fixation element into a lumen thereof, the insertion element insertable in a screwing motion across the soft tissue tear and positionable with a portion between a distal end and a proximal end bridging the tear, the insertion element removable in a reverse screwing motion, leaving the fixation element positioned in bridging relation across the tear;
   a cannula adapted to pierce a skin of a patient and into the soft tissue proximal of the tear, the cannula adapted to admit the insertion element therethrough for positioning across the tear; and
   a guide needle having a diameter smaller than a bore of the insertion element and insertable across a soft tissue tear, the insertion element insertable across the tear in encompassing relation to the needle.

5. An orthopedic system for fixation of a soft tissue tear comprising:
   a generally helical fixation element comprising a substantially flexible core and a shape-retaining material in overlying relation thereto, the shape-retaining material comprising a bioresorbable material; and
   a hollow, generally helical insertion element dimensioned to admit at least a distal portion of the fixation element into a lumen thereof, the insertion element insertable in a screwing motion across the soft tissue tear and positionable with a portion between a distal end and a proximal end bridging the tear, the insertion element removable in a reverse screwing motion, leaving the fixation element positioned in bridging relation across the tear.

6. A method of fixating a soft tissue tear comprising the steps of:
   inserting a generally helical insertion element across a soft tissue tear in a screwing motion, the insertion element having a first pitch along a distal portion, a second pitch along a central portion, and a third pitch along a proximal portion, the second pitch larger than the first and the third pitches, the central portion positioned across the tear;
   inserting at least a distal portion of a generally helical, flexible fixation element into a lumen of the insertion element, the fixation element biased to a predetermined pitch less than the insertion element second pitch; and
   withdrawing the insertion element in an unscrewing motion, leaving the fixation element in position across the tear, contracted to the predetermined pitch and drawing two sides of the tear together.

7. The method recited in claim 6, further comprising the step of inserting a needle across the tear prior to inserting the insertion element, and wherein the insertion element inserting step comprises inserting the insertion element over the needle, and wherein the withdrawing step further comprises withdrawing the needle.

8. The method recited in claim 6, further comprising the step, prior to the insertion element inserting step, of inserting a guide needle having a diameter smaller than a bore of the insertion element across the soft tissue tear, and wherein the insertion element inserting step comprises inserting the insertion element across the tear in encompassing relation to the needle.

9. The method recited in claim 6, further comprising the steps of, prior to the insertion element inserting step, of:
   inserting a cannula through a skin of a patient and into the soft tissue proximal of the tear; and
   admitting the insertion element through a bore of the cannula.

10. The method recited in claim 9, further comprising the step, prior to the insertion element inserting step, of inserting a guide needle having a diameter smaller than a bore of the insertion element across the soft tissue tear, and wherein the insertion element inserting step comprises inserting the insertion element across the tear in encompassing relation to the needle.

11. The method recited in claim 6, wherein the fixation element comprises a substantially flexible core and a shape-retaining material in overlying relation thereto, the shape-retaining material comprising a bioresorbable material.

12. A method for fixation of a soft tissue tear comprising the steps of:
   inserting a needle having a pointed tip in bridging relation to a soft tissue tear;
   inserting a generally helical fixation element into the soft tissue in a screwing motion, a lumen of the helical element in surrounding relation to the needle; and
   withdrawing the needle, leaving the helical element in bridging relation to the tear.

13. The method recited in claim 12, further comprising the steps of, prior to the needle inserting step, of:
   inserting a cannula through a skin of a patient and into the soft tissue proximal of the tear; and
   admitting the insertion element through a bore of the cannula.

14. The method recited in claim 12, wherein the fixation element comprises a substantially flexible core and a shape-retaining material in overlying relation thereto, the shape-retaining material comprising a bioresorbable material.

* * * * *